United States Patent [19]

Dawson et al.

[11] 4,013,801
[45] Mar. 22, 1977

[54] EDIBLES SWEETENED WITH FLAVANONES

[75] Inventors: Daniel J. Dawson; Kenneth M. Otteson, both of Menlo Park; C. Thomas Seitz, Mountain View, all of Calif.

[73] Assignee: Dynapol Corporation, Calif.

[22] Filed: Feb. 13, 1976

[21] Appl. No.: 657,906

[52] U.S. Cl. .............................. 426/548; 426/590; 424/283; 424/49; 260/345.2

[51] Int. Cl.² .......................................... A23L 1/236

[58] Field of Search ............ 426/548, 590; 424/49, 424/283; 260/345.2

[56] References Cited

UNITED STATES PATENTS

| | | | |
|---|---|---|---|
| 3,864,362 | 2/1975 | Feuer et al. | 424/283 X |
| 3,907,830 | 9/1975 | Feuer et al. | 424/283 X |
| 3,949,085 | 4/1976 | Feuer et al. | 424/283 |
| 3,974,299 | 8/1976 | Crosby et al. | 426/548 |

FOREIGN PATENTS OR APPLICATIONS 1,518,006  1/1969  Germany ........................ 260/345.2

OTHER PUBLICATIONS

Horowitz, et al, *J. Agr. Food Chem.*, vol. 17, No. 4, (1969) pp. 696–700.

*Primary Examiner*—A. Louis Monacell
*Assistant Examiner*—Esther L. Massung
*Attorney, Agent, or Firm*—William H. Benz

[57] ABSTRACT

Edible materials including foods, beverages and oral pharmaceuticals are sweetened by the addition of a sweetening amount in the range of from about 0.002% to 1% by weight (basis edible material) of flavanone represented by the structural formula

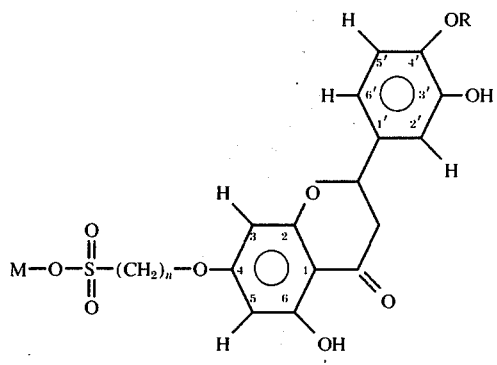

wherein R is a lower alkyl of from one to three carbon atoms inclusive, $n$ is an integer of from one to three inclusive and M is hydrogen or a physiologically acceptable metal cation.

19 Claims, No Drawings

EDIBLES SWEETENED WITH FLAVANONES

BACKGROUND OF THE INVENTION

This invention relates to the sweetening of edibles such as foods, beverages and oral pharmaceuticals. More particularly, it relates to the use of certain flavanones as sweeteners for flavanones.

There is an ever-growing need for acceptable sugar substitutes. Mankind's craving for sweetness is well known as are the problems linked to the use of sucrose and other "sugar" materials to satisfy these desires. These problems include obesity, dental caries, and in predisposed individuals—diabeties, to name but three examples. A range of nonsugar sweeteners have been discovered and employed with varying degrees of success over the last half century. The present invention teaches the use of certain flavanones as sweeteners. It is believed to break new ground and add a whole new class of materials to the realm of nonsugar sweeteners as flavanones studied as flavorants heretofore have been reported to have bitter tastes or to be tasteless. As a result, some prior studied flavanones such as naringin (the principle bitter substance in grapefruit peels) are employed commercially as bittering agents. One flavanone, hesperetin, is reported by one investigator, Horowitz, *Biochemistry of Phenolic Compounds* (Academic Press, 1964, Pages 555–556) as being slightly sweet. No flavanone materials are known to have been reported to have useful sweetness. Two additional references which discuss flavanone taste properties are: Horowitz and Gentile, *Agr. and Food Chem.* Volume 17, No. 4, page 696 (1969) and Kamuja et al *Agr. Biol. Chem.*, Volume 39, page 1757 (1975).

STATEMENT OF THE INVENTION

It has now been found that a sweet flavor can be imparted to edible materials by adding thereto an effective sweetening amount in the range of from 0.002% by weight to about 1% by weight of certain flavanone compounds. These flavanones are represented by General Structural Formula I.

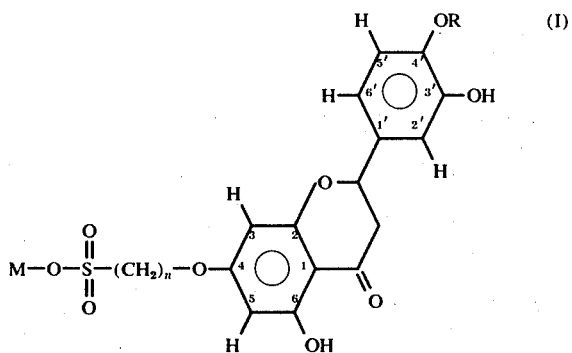

wherein R is a lower alkyl of from one to three carbon atoms inclusive, $n$ is an integer of from one to three inclusive and M is hydrogen or a physiologically acceptable metal cation. These flavanones are characterized by an absence of glycoside residues in their structure, by substantial water-solubility, by organoleptic properties similar to those of sucrose, and by sweetness as much as several hundred times that of sucrose.

DETAILED DESCRIPTION OF THE INVENTION

Throughout this Detailed Description, reference is made to the positions of various substituents on the flavanone molecules. These positions are numbered and will be referenced in accordance with General Formula I.

The Flavanones

The flavanones employed in this invention contain two hydroxyl groups at the 6 and 3' positions. They contain hydrogens at the 3, 5, 2', 5', and 6' positions. At the 4' position they contain a lower saturated alkoxy group of from one to three carbon atoms, that is one selected from the group of methoxy, ethoxy and the propoxies; preferably the 4'-substituent is a methoxy or n-propoxy, and most preferably a methoxy. At the 4 position they contain a substituted oxy group. This oxygen atom is substituted with an alkyl sulfonate anion to yield an oxyalkylsulfonate anion of from one to three carbon atoms inclusive. The alkyl sulfonate anion is present as the acid or as a salt with a physiologically acceptable metal cation. As used herein, a "physiologically acceptable metal cation" is defined to include $Li^+$ and the cations of the third and fourth period metals which are nontoxic, i.e., $Na^+$, $K^+$, $Mg^{+2}$, $Ca^{+2}$, $Al^{+3}$, $Mn^{+2}$, $Fe^{+3}$ and $Zn^{+2}$. Preferred metal cations are the cations of the third and fourth period group I and II metals, i.e., $Na^+$, $K^+$, $Mg^{+2}$ and $Ca^{+2}$.

Preparation of Flavanones

The materials of General Formula I are conveniently formed, in a general sense, by the mechanism of alkylating the 4-hydroxyl group of the known compound hesperetin

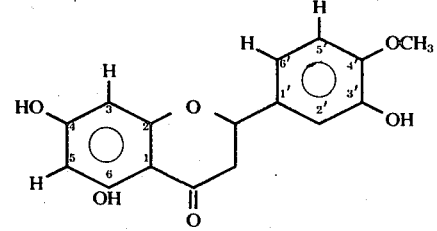

(or a 4'-ethoxy or propoxy equivalent of hesperetin) with a one to three carbon alkyl sulfonate group.

In the case when $n$ in General Formula I equals 1, sodium iodomethanesulfonate or the pyrrolidine amide of chloromethylsulfonic acid are suitable agents with which to effect alkylation. More specifically, by the first route hesperetin or a 4'-ethoxy or methoxy equivalent can be reacted with the sodium salt of iodomethanesulfonic acid in the presence of potassium carbonate in DMF at reflux for several hours to yield at the 4 position of the hesperetin (or its equivalent) a sulfo-substituted methoxy. In the second route, chloromethylsulfenyl chloride is first prepared by contacting trithiane,

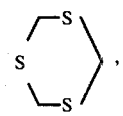

with molecular chlorine. The chloromethylsulfenyl chloride can then be reacted with pyrrolidine,

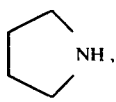

to form

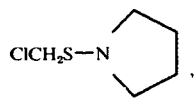

which will facilely alkylate hesperetin (or the 4' ethoxy or propoxy equivalent) in the 4 position and, after S oxidation and sulfonamide hydrolysis, yields the desired sulfomethoxy flavanone.

In the case where $n$ in General Formula I equals 2, the alkylating agent can be $Br—CH_2—CH_2—SO_3^-Na^+$, or the like. This material, when contacted with an equimolar amount of hesperetin (or a 4' ethoxy or propoxy equivalent) in the presence of potassium carbonate or a similar weak base, in DMF, DMSO, or the like, preferentially alkylates the 4-hydroxyl. There is, of course, as with all these reactions, some alkylation of other hydroxyls. The various materials may be separated and the desired 4-alkylate recovered by fractional crystallization or chromatography techniques.

In the case where $n$ in General Formula I equals 3, propane sultone is the alkylating agent of choice, as it directly attaches the required three carbon alkyl group and the $SO_3^-$ in one step. This alkylation is carried out in DMF, methyl cellasolve, DMSO or a like dipolar aprotic solvent in the presence of sodium carbonate or a like weak base.

All of these alkylations can be carried out under relatively mild conditions, such as about room temperature for 24 to 72 hours. It is also possible to use elevated temperatures, such as up to about 100° C with corresponding shorter reaction times such as as short as about 1 hour.

The products of any of these reactions can be purified and isolated by fractional crystallization, thin layer chromatography and the like, as desired.

The preparative schemes set forth above depict sodium as the cation. By varying starting materials among potassium, calcium and the like salts, a variety of metal cations can be incorporated. Treatment with $H^+$ can yield the acid. Also, it is possible to change cations by passage of a solution of flavanone over an appropriately charged ion exchange resin or often by merely adding an excess of the desired cation to a solution of flavanone and precipitating the desired salt.

These preparations will be further set forth in the examples. These are not intended to be limiting as other methods equivalent to those skilled in the art of organic synthesis may be employed as well.

Forming Sweetened Edibles

Edible materials such as foods, beverages, medicines and the like are sweetened by the addition of an effective amount of these certain flavanones.

The flavanones represented by Formula I can be prepared in a variety of forms suitable for the utilization of sweetening agents. Typical forms which can be employed are: solid forms such as powders, tablets, and granules; and liquid forms such as solutions, suspensions, syrups, and emulsions. These forms can consist of the compounds of Formula I aparts from or in association with nontoxic sweetening agent carriers, i.e., nontoxic substances commonly employed in association with sweetening agents. Such suitable carriers include liquids such as water, ethanol, sorbitol, glycerol, citric acid, corn oil, peanut oil, soybean oil, sesame oil, propylene glycol, corn syrup, maple syrup, and liquid paraffin; and solids such as lactose, cellulose, starch, dextrin and other modified starches, calcium phosphate and calcium sulfate. Obviously incompatible for use with the sweetening agents of Formula I would be toxic carriers such as methanol and dimethyl sulfoxide.

The flavanones are added to the edible material by mixing methods known in the art. They may be used alone or as the primary or secondary sweetener in the final composition; with a natural sweetener such as sucrose, or another synthetic sweetener such as saccharin or cyclamate also being added. Combinations of two or more of the present flavanones may be used, if desired.

Examples of specific edible materials which can be sweetened by the addition of a flavanone of Formula I or by a novel combination of the material of Formula I with a known sweetening agent include: fruits, vegetables, and juices; meat products such as bacon and sausage; egg products; fruit concentrates; gelatins and gelatin-like products such as jelly and preserves; milk products such as ice cream, sour cream and sherbet; icings; syrups; grain products such as bread, cereals, pasta and cake mixes; fish; cheese products; nut products; beverages such as coffee, tea, noncarbonated and carbonated soft drinks, beers, wines and liquors; and confections such as candy and chewing gums.

Additional illustrations of the type of commercial products in which the sweetening agents or combinations thereof with known sweetening agents can be used are granulated mixes which upon reconstitution with water provide noncarbonated drinks; instant pudding mixes; instant coffee and tea; pet foods; livestock feed; tobacco and consumable toiletries such as mouth washes and toothpastes, as well as proprietary and nonproprietary pharmaceutical preparations.

The amount of flavanone employed can vary widely, just as the amount of natural sugar sweetener employed varies from person to person and from application to application.

An "effective amount" of flavanone is employed. An "effective amount" is defined to be that amount which imparts to the edible the degree of sweetness desired. As a general rule, this "effective amount" will range from about 1/50 to 1/500th the weight of sucrose required to obtain the same degree of sweetness. Thus, addition of from about 0.002% to about 1.0% by weight (basis edible material) may be usefully employed with additions of from about 0.003 to about 0.5% by weight are preferred. The present flavanones offer the advantage that their substantial water solubility permits such addition to most food systems.

These flavanones, their preparation and their use as sweeteners are further described in the following Examples. These are to illustrate the invention and are not to be construed as limitations on this invention, which is instead defined by the appended claims.

EXAMPLE I

A. Preparation of

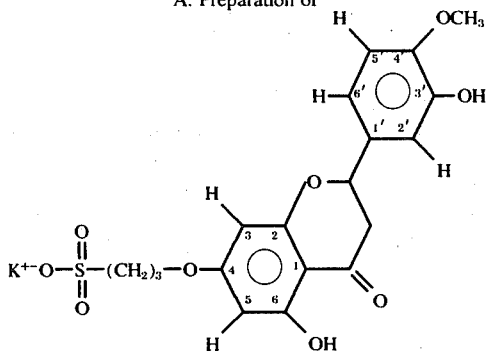

A. Hydrolysis of Hesperidin to Hesperetin

To a 12-liter three-neck round bottom flask equipped with an overhead stirrer was added 466.8 g (11.7 moles) of sodium hydroxide followed by 4650 ml of water. After the solution was cooled in an ice bath and blanketed with argon, 3 kg (4.08 moles, 83% pure) of hesperidin (Sunkist) was added portionwise to give a clear dark orange solution. A 22-liter reaction flask with an overhead stirrer, a reflux condenser, and a heating mantle was charged with 8.5 l of water, 1.5 l of 2-methoxyethanol, and 2.04 l of concentrated aqueous hydrochloric acid (12 N, 24.5 moles). This solution was stirred vigorously and heated to reflux under argon; the hesperidin solution was pumped (peristaltic pump with Tygon tubing) into the boiling acid solution over 35 min. The resulting suspension was heated at reflux for an additonal 30 min, cooled to room temperature with an ice bath, filtered (coarse sintered glass), washed with three 4-l portions of water, and sucked dry to give 2674 g of a wet cake containing 1352 g ($\leq$ 91% pure) of crude hesperetin. This material was used directly in the next reaction.

B. Sulfopropylation of Hesperetin

A solution of 2746 g of the wet cake from the previous reaction (containing 1344 g, $\leq$ 4.05 moles, of crude hesperetin) in 6 l of a 2-methoxyethanol was added to a 12-liter three-neck round bottom flask equipped with an overhead stirrer, argon bleed, and a pH probe. Water (1.2 l) and 2-methoxyethanol (500 ml) were added to the flask and the pH was brought to 8.5 by the addition of ~400 ml 6.0 N aqueous potassium hydroxide. A slow stream of argon was passed through the flask and 760 g (6.22 moles, ~1.5 eq) of propane sultone (Aldrich) was added in one portion. The pH was maintained automatically at 8.50 ±.01 for 20 hr. by the addition of 538 ml 6 N aqueous potassium hydroxide as needed (total base used was 938 ml of 6 N or 5.63 moles). At this time, HPLC demonstrated that there was very little hesperetin left, along with an equal but growing amount of an unidentified side product. The reaction was stopped by allowing the pH to fall.

After sitting at room temperature for 2 days, the solution had a pH of 3; this reaction mixture was treated with 6 N potassium hydroxide (30 ml) to raise the pH to 7.2, then heated at reflux for 1 hour to destroy any excess propane sultone. The solution was later warmed to 55° C in a 22-liter reaction flask, diluted with 10.25 l of isopropanol, and allowed to form a precipitate composed of various impurities overnight. After filtration, the solids (328.7 g) were set aside; the filtrate was partially stripped (15.25 l removed), diluted with 8 l $H_2O$, filtered with 200 g of Celite, extracted with five 1-gallon portions of ethyl acetate to remove other impurities, and briefly stripped to remove the ethyl acetate residue (~1 l removed). The filtrate was put through an exhaustive series of crystallizations and recrystallizations to finally yield 832 g (44% yield from hesperidin) of sulfopropylated hesperetin as a white solid.

C. Use of the Flavanone

The product made in accordance with Part B was dissolved in water at a 400 ppm concentration. It was tasted by a group of volunteers who reported that it had sweetness equivalent to that of a 85,000 ppm sucrose solution and that in flavor character it was very sugar-like. This would indicate a sweetening power of 200–300 × sucrose. The flavanone is then added to a variety of edible materials as a sweetener as shown in Table I.

TABLE I

Use of Flavanone as Sweetener

| Edible Substrate | Amount of Flavanone added, ppm wt basis Edible Substrate | Method of Addition | Other Sweetness Present |
|---|---|---|---|
| Soft drink | 500 ppm | dissolving | none |
| Soft drink | 200 ppm | dissolving | sucrose; 5% |
| Soft drink | 200 ppm | dissolving | saccharine, 50 ppm |
| Soft drink concentrate | 8,000 ppm | dissolving | none |
| Soft drink powder | 10,000 ppm | dry mixing | |
| Gelatin dessert powder | 5,000 ppm | dry mixing | sucrose 25% |
| Cough elixer | 400 ppm | dissolving | none |
| Toothpaste | 800 ppm | dissolving | none |
| Cake mix | 800 ppm | dry mixing | none |
| Chewing gum | 500 ppm | dry mixing | none |
| Chewing gum | 500 ppm | dissolving | saccharine, 200 ppm |
| Soft drink | °ppm | dissolving | sucrose, 8% |

EXAMPLE II

A. Preparation of

-continued

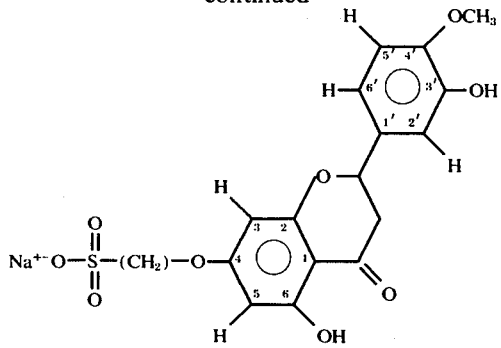

Following the general teachings of Douglass et al, *J. Org. Chem.* 15, 795-9 (1950), purified trithiane,

28 grams, and methylene chloride reaction solvent are placed in a vessel and chilled to 0° C. Chlorine gas (16 grams) is slowly passed into the vessel with stirring while maintaining the 0° C temperature. After 3 hours, the vessel is permitted to warm to room temperature and unreacted chlorine is removed.

The reaction mixture is warmed to about 50° C and vacuum is applied, causing chloromethylsulfenyl chloride ($ClCH_2SCl$) to distill overhead.

Chloromethylsulfenyl chloride (one equivalent) is dissolved in benzene and two equivalents of pyrrolidine is gradually added with stirring. The mixture is stirred at room temperature for 1 hour. Benzene is stripped and a product

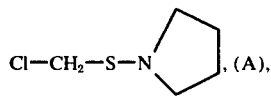

is isolated by distillation.

A solution of 3.0 g of hesperetin (Sigma Chemical Co.) in 20 ml of dimethylformamide is prepared. 0.7 Grams of anhydrous potassium bicarbonate is added followed by 4.6 g of (A). The mixture is stirred overnight, at which time excess peracetic acid is added in acetic acid solvent and stirred for 12 hours to form

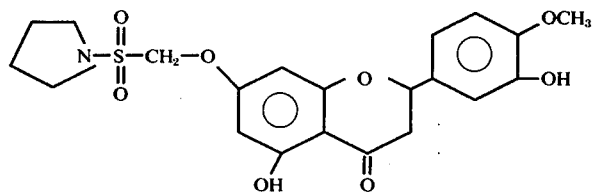

Water is then added and the mixture is stirred at room temperature for an hour to oxidatively hydrolyze and convert the sulfonamide to the flavanone sulfonate, Sodium bisulfite is added to consume unreacted peracetic acid. Following evaporation of volatile materials, the flavanone sulfonate as the sodium salt is obtained pure by crystallization from water.

B. Use of the Flavanone

An aqueous solution of the flavanone (400 ppm) is prepared and tasted and found to be sweet. The flavanone is then added (400 ppm) to a soft drink base, to a chewing gum and a toothpaste. It sweetens these materials.

EXAMPLE III

A. Preparation of

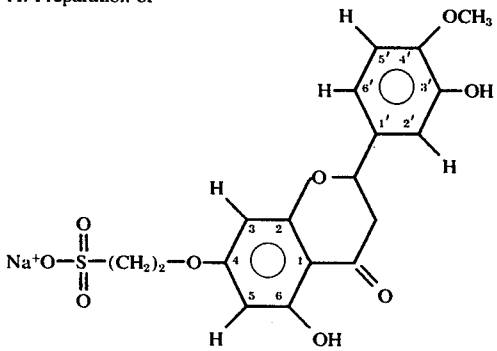

72 Milligrams of 50% sodium hydride is washed with hexane. Seven milliliters of anhydrous dimethylsulfoxide is added under an argon cap. Next, 302 mg of hesperetin is slowly added in about 1ml of dimethylsulfoxide. The mixture is reacted at room temperature and then at 50° C from about an hour. Then Br—$CH_2$—$CH_2$—$SO_3Na$ (253 mg) in dimethylsulfoxide is added and the mixture is stirred overnight under argon at room temperature. Solvent is then stripped off and the product is extracted with ethylacetate. The desired flavanone is crystallized from water to purify.

B. Use of the Flavanone

The material of Part A is dissolved in a cola beverage base dispersed in a gelatin dessert mix and added to fruit preserves. In each application it increases the sweetness of the edible material.

EXAMPLE IV

This example deals with the preparation of additional metal ion salts of the flavanones.

A sample of the propoxysulfonate flavanone potassium salt prepared in Part B of Example I is placed on an anion exchange column such as the polyalkylamonium chloride column marketed as Bio Rex 5. Elution is begun with a 1:1:1 acetonitrite-ethanol-water mixture. Then a gradient of 1 molar aqueous lithium chloride is added. This causes the lithium salt of the propoxysulfonate flavanone to elute. The lithium sulfonate salt is recovered from the eluent by crystallization. This procedure is repeated using sodium chloride and the methoxy and methoxy flavanones of Examples II and III with equivalent results. These materials are added to edibles as well and impart sweetness thereto.

EXAMPLE V

This example deals with the preparation of alkaline earth metal salts of the flavanones. Basically, it involves adding an excess of the alkaline earth cation to a solution of the flavanones and separating the alkaline earth metal salt by crystallization.

An aqueous solution of the flavanone potassium salt prepared in Example I is prepared. A saturated solution of calcium chloride is added. The combined solution is evaporated until crystals form. These are the calcium salt of the flavanone prepared in Example I.

EXAMPLE VI

This example deals with the preparation of the free acids of the flavanones (i.e., when M equals hydrogen).

A solution of the potassium salt of the flavanone of Example I is prepared and placed on a strongly acidic cation exchange resin column such as Rohm and Haas Amberlite IR-120 strongly acidic sulfonated polystyrene.

Water is passed into the column and the eluent is collected. The eluent is freeze-dyed to remove all water and to yield the desired free acid as a solid product.

EXAMPLE VII

This example sets forth the preparation of 4'-ethoxy and propoxy equivalents of the flavanone of Example I. These materials are formed by condensing the appropriate benzaldehydes and acetophenones to chalcones and then closing under acidic conditions to flavanones.

A. Preparation of the acetophenone

To a solution of 1.68g of phloroacetophenone and 12.7 g of benzyl chloride in 20 ml of DMF is added 5.53 g of anhydrous $K_2CO_3$. The mixture is stirred for 16 hours at 65° under argon. The mixture is diluted with 100 ml of 5% NaCl and extracted with ethyl acetate (2 × 50 ml). The extracts are washed with 5% NaCl and 2% NaOH, dried over $MgSO_4$ and concentrated to a red oil which is purified on a dry 250 g silica gel columning $CCl_4$ as eluent. This yields 2,4,6-tribenzyloxyacetophenone as a yellow oil.

B. Preparation of aldehydes

To a solution of 14.2 g of 3,4-dihydroxybenzaldehyde, 10.9 g of ethyl bromide, and 14.98 g sodium iodide in 150 ml DMF is added 13.82 g of anhydrous $K_2CO_3$. After 16 hours at R.T., tlc and VPC analyses indicate substantial completion of reaction.

The reaction mixture is then diluted with 500 ml 5% NaCl solution and extracted with ether (2 × 250 ml). The combined ether extracts are washed with 5% NaCl solution and then with 5% NaOH solution. The combined base extracts are acidified with concentrated HCl while cooling in an ice bath. After standing overnight at 0°, a brown precipitate is filtered and washed with water. Recrystallization from EtOH—$H_2O$ yeilds 3-hydroxy-4-ethoxy-benzaldehyde as off-white needles.

To a solution of 1.66 g of 3-hydroxy-4-ethoxy-benzaldehyde and 2.53 g of benzyl chloride in 20 ml DMF is added 2.76 g (20 mmoles) of anhydrous $K_2CO_3$. After stirring under argon for 21 hours, the reaction is checked by tlc and found to be complete. The reaction mixture is diluted with 60 ml 5% NaCl solution and extracted with EtOAc (50 ml). The combined extracts are washed with 5% NaCl solution, 1% NaOH solution, dried over $MgSO_4$ and concentrated yielding a yellow oil. After removal of volatile components at reduced pressure, the residue is recrystallized from aqueous ethanol yielding white needles of 3-benzyloxy-4-ethoxybenzaldehyde.

This aldehyde preparation is essentially repeated substituting n-propyl iodide for ethyl iodide in the starting materials. This results in 3-benzyloxy-4-n-propoxybenzaldehyde as a second aldehyde product.

C. Preparation of chalcones

To a solution of 2.19 g of 2,4,6-tribenzyloxyacetophenone and 1.28 g of 3-benzyloxy-4-ethoxybenzaldehyde in 5.0 ml warm absolute ethanol is added 7.5 ml of 60% KOH. The resulting reaction mixture is stirred at ambient temperature overnight resulting in the formation of a gummy precipitate. The reaction mixture is then dumped into 30 ml of water and extracted with ether (2 × 25 ml), the combined portions of which are dried over $MgSO_4$ and concentrated yielding a yellow solid. TLC analysis indicates the formation of a sole product and complete consumption of both starting materials. Recrystallization from EtOAc—MeOH yields yellow needles of 2,4,6,3'-tetrabenzyloxy-4'-ethoxychalcone, i.e.,

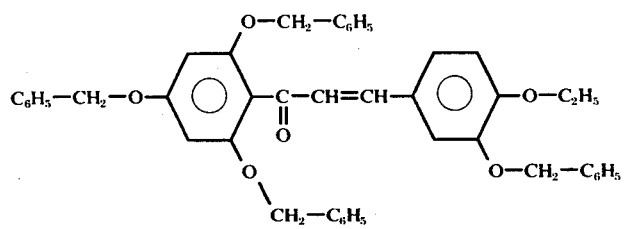

This reaction is repeated using the propoxy aldehyde in place of the ethoxy aldehyde. The product which results is the corresponding 4'-propoxychalcone.

D. Cyclization to flavanones

To a solution of 1.35 g of the ethoxy chalcone of Part C in 20 ml of acetic acid is added 5.45 g of 45% (w) hydroiodic acid. The mixture is stirred at room temperature for 24 hours and then dumped into 45 ml of water and extracted with EtOAc (3 × 25 ml). The combined extracts are washed with water (6 × 100 ml) and concentrated to dryness. The resulting flavanone product,

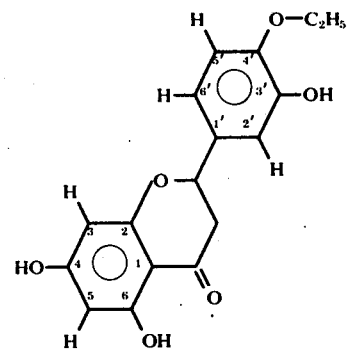

is recovered and purified by recrystallization from ethanol-water.

When this reaction is repeated using the 4'-propoxy chalcone of Part C the corresponding 4-propoxy flavanone results.

E. Alkylation

The two flavanones of Part D are serially substituted for hesperetin in the reaction and workup of Part A of Example I. This results in the formation and recovery of first the 4-ethoxy equivalent of the product of Example I and second the 4'-n-propoxy equivalent of the product of Example I, i.e.,

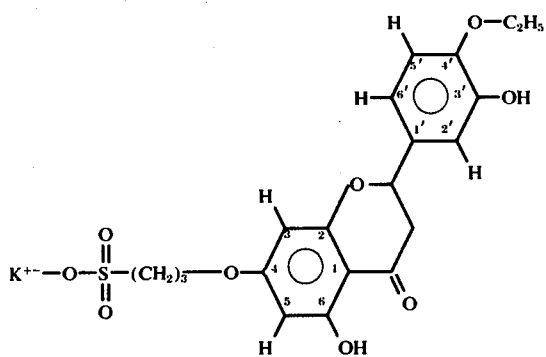

-continued
and

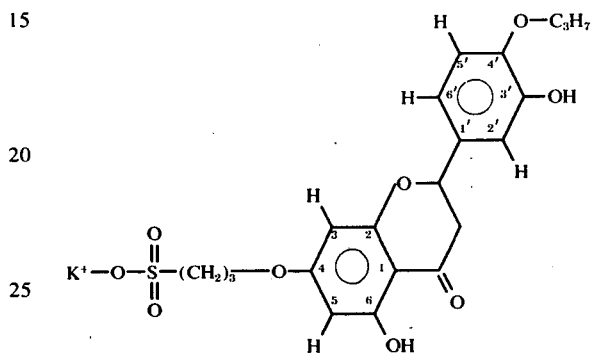

It will be apparent to those skilled in the art to likewise substitute the two flavanones of Part D of this example in the preparations of Examples II and III and the reactions of Examples IV, V and VI.

What is claimed is:

1. A sweetened edible composition comprising an edible material having admixed therewith a sweetening amount in the range of from about 0.002% to about 1% by weight basis material of flavanone represented by the structural formula

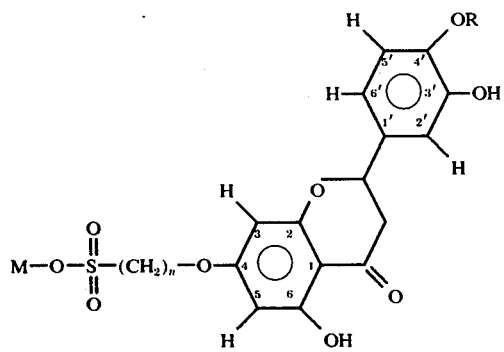

wherein R is a lower alkyl of from one to three carbon atoms inclusive, $n$ is an integer of from one to three inclusive and M is hydrogen or a physiologically acceptable metal cation.

2. The edible composition of claim 1 wherein the edible material is a foodstuff.

3. The edible composition of claim 1 wherein the edible material is a beverage.

4. The edible composition of claim 1 wherein the edible material is an oral pharmaceutical.

5. The edible composition of claim 1, wherein $n$ has a value of 1 and R is methyl.

6. The edible composition compound of claim 1, wherein $n$ has a value of 1 and R is ethyl.

7. The edible composition of claim 1, wherein $n$ has a value of 1 and R is n-propyl.

8. The edible composition of claim 1, wherein $n$ has a value of 2 and R is methyl.

9. The edible composition of claim 1, wherein $n$ has a value of 2 and R is ethyl.

10. The edible composition compound of claim 1, wherein $n$ has a value of 2 and R is n-propyl.

11. The edible composition of claim 1, wherein $n$ has a value of 3 and R is methyl.

12. The edible composition of claim 1, wherein $n$ has a value of 3 and R is ethyl.

13. The edible composition of claim 1, wherein $n$ has a value of 3 and R is n-propyl.

14. The edible composition of claim 5, wherein M is potassium ion.

15. The edible composition of claim 5, wherein M is hydrogen ion.

16. The edible composition of claim 8, wherein M is potassium ion.

17. The edible composition of claim 8, wherein M is hydrogen ion.

18. The edible composition of claim 11, wherein M is potassium ion.

19. The edible composition of claim 11, wherein M is hydrogen ion.

* * * * *